United States Patent [19]

VanAtten

[11] Patent Number: 5,236,934
[45] Date of Patent: Aug. 17, 1993

[54] 1,2,3,4-TETRAHYDROISOQUINOLINES USEFUL IN THE TREATMENT OF CNS DISORDERS

[75] Inventor: Mary K. VanAtten, Wilmington, Del.

[73] Assignee: E. I. Du Pont de Nemours and Company, Wilmington, Del.

[21] Appl. No.: 935,509

[22] Filed: Aug. 26, 1992

[51] Int. Cl.$^5$ ............... A61H 31/47; C07D 217/16
[52] U.S. Cl. ............................. 514/307; 514/310; 546/143; 546/146; 546/147
[58] Field of Search ............ 546/143, 144, 146, 147; 514/307, 310

[56] References Cited

U.S. PATENT DOCUMENTS

| | | | |
|---|---|---|---|
| 4,344,949 | 8/1982 | Hoefla et al. | 546/147 |
| 4,812,462 | 3/1989 | Blankely et al. | 514/303 |
| 5,059,608 | 10/1991 | Takasugi et al. | 514/307 |
| 5,091,390 | 2/1992 | Ardecky et al. | 514/303 |

FOREIGN PATENT DOCUMENTS 0401676  12/1990  European Pat. Off. .

OTHER PUBLICATIONS

Niopas, "Pharm. Delt., Epistem. Ekdosis", vol. 10, No. 1, 1984, pp. 1–15.
"Chemical Abstracts" version vol. 104, 1986, p. 688.

*Primary Examiner*—C. Warren Ivy
*Assistant Examiner*—James H. Turnipseed

[57] ABSTRACT

Provided are 1,2,3,4-tetrahydroisoquinolines, methods for preparing them, pharmaceutical compositions containing them, and methods of using them to treat disorders of mammals mediated by $AT_2$ receptors in the central nervous system.

17 Claims, No Drawings

1,2,3,4-TETRAHYDROISOQUINOLINES USEFUL IN THE TREATMENT OF CNS DISORDERS

FIELD OF THE INVENTION

This invention relates to specific inhibitors of angiotensin II (AII) binding to angiotensin-II subtype-2 (AT$_2$) receptors.

BACKGROUND OF THE INVENTION

Angiotensin II (AII) is an octapeptide hormone which is a component of the renin-angiotensin system. In addition to being a circulating hormone which affects the cardiovascular system, the adrenal cortex, the peripheral autonomic nervous system, and the kidneys, AII is also known to affect the central nervous system. AII is now believed to act as a neuropeptide in the central nervous system (CNS) and may modulate the release and subsequent action of other neurotransmitters (Unger et al. (1988) *Circulation* 77 (Suppl. I):40–54).

Specific high affinity receptors for AII have been identified and localized in different regions of the CNS (Mann (1982) *Exp. Brain Res.* 4 (Suppl):242). Stimulation of AII receptors in the CNS elicits a complex, but highly reproducible and concerted pattern of behavioral, cardiovascular, and endocrine responses (Fitzsimons (1980) *Rev. Physiol. Biochem. Pharmacol*, 87:117). These include CNS-induced elevation of blood pressure, increased drinking and sodium appetite, and release of antidiuretic hormone, oxytocin, luteinizing hormone, and prolactin (Scholken et al. (1982) *Experientia* 38:469). The CNS effects of AII could lead to hypertension and other cardiovascular diseases through inhibition of the baroreceptor reflex, increase in salt consumption, volume expansion, and increased peripheral resistance. Besides the cardiovascular system, AII may also influence the reproductive system and other brain functions, such as memory (Koller et al. (1975) *Neuroscience Lett.* 14:71–75).

The major functions of AII in the CNS can be classified into three groups which may share, at least in part, overlapping mechanisms of action. The first major function of AII in the CNS is regulation of body fluid volume in response to hypovolemia, involving, for example, regulation of thirst, blood pressure increases, vasopressin release, sodium appetite increase, adrenocorticotropic hormone (ACTH) release, and aldosterone release (Unger et al. (1988) *Circulation* 77 (Suppl I):-40–54, and references cited therein). This CNS function of AII is closely related to the peripheral role of AII in hypertension.

A second function of AII in the CNS, although less well defined, is the regulation of gonadotrophic hormone releasing hormones and pituitary hormones during the reproductive cycle and pregnancy (Unger et al., supra).

A third possible CNS function of AII is a synaptic function. AII appears to interact with neurotransmitters such as acetylcholine (ACH), catecholamines, serotonin, and other neuroactive peptides (Unger et al., supra). Although the amount of data supporting this CNS function of AII is limited, published results suggest that increased AII activity in the brain exerts an inhibitory effect on cholinergic neurons resulting in impaired cognitive performance. Therefore, compounds that inhibit AII biosynthesis, or block AII receptor activation may enhance cognition.

The role of peptides in learning and memory was initially investigated by D. DeWied in the late 1960's and early 1970's. This led Morgan and Routtenberg *Science* (1977) 196:87–89) to investigate the role of AII in mediating retention of a passive avoidance (PA) response in rats. These authors demonstrated that rats injected with AII into the dorsal neostriatum, a brain area that has a high concentration of AII as well as precursors and metabolic enzymes for AII biosynthesis, showed a disruption in retention of a PA response. The authors demonstrated specificity of the response in terms of both the location in the brain, and the peptide used (unlike AII, thyrotropin releasing hormone or lysine-8-vasopressin had no effect). This study showed that increased AII in the dorsal neostriatum results in a cognitive impairment which is most likely related to AII modulation of neuronal activity that is necessary for consolidation of newly acquired information.

A different approach for investigating the behavioral effects of AII in the CNS was taken by Koller et al. (*Neuroscience Letters* (1975) 14:71–75). These authors injected renin into the lateral ventricle of the brain (IVT) and measured increases in AII in cerebrospinal fluid (CSF); AII levels increased from 40 to about 5000 fmol per mL. This increase in AII was accompanied by a disruption of avoidance learning. These results suggested that renin-stimulated biosynthesis of AII could disrupt memory. Administration into the IVT of the angiotensin converting enzyme (ACE) inhibitor SQ 14225 (captopril) prior to the renin injection, prevented the renin-induced avoidance disruption. Applicants have also found that renin administered IVT produces a dose-related amnesia in a PA task, which is prevented by IVT administration of the ACE inhibitor captopril. These results suggest that increased AII levels in the brain lead to a disruption of learned avoidance. This amnesia can be achieved by direct administration into a discrete brain area of either AII or renin, an enzyme involved in endogenous AII biosynthesis.

In the literature on the neuropathology and neurochemistry of Alzheimer's disease (AD), there are two reports of altered levels of dipeptidyl carboxypeptidase (angiotensin-converting enzyme, ACE) in human CSF and brain tissue. Arrequi et al. (*J. Neurochemistry* (1982) 38:1490–1492) found increased ACE activity in the hippocampus, parahippocampal gyrus, frontal cortex, and caudate nucleus in AD patients. Zubenko et al. (*Biol. Psych.* 21:1365–1385 (1986) found a correlation between levels of ACE in the CSF and the severity of AD. Whether the alterations in ACE cause the progression of dementia or are correlates of the disease progress remains unknown.

Recent evidence that inhibition of ACE can have a modulatory effect on learning and memory was reported by Usinger et al. (*Drug Dev. Research* 14:315–324 (1988); also European Patent Application, EP 307,872 to Hoechst, published Mar. 22, 1989).

Similar results were reported by Costall et al. (*Pharmacol. Biochem. Behav.* 33:573–579 (1989)) using the ACE inhibitor captopril. These authors demonstrated that subchronic treatment with captopril increased the rate of acquisition of light/dark habituation performance. Further, anticholinergic scopolamine-induced disruption of performance in this test model was prevented by daily treatment with captopril.

The ACE inhibitor SQ 29852 has also been reported to provide protective effects on memory of previously learned tasks and to ameliorate, at least in part, an anticholinergic effect on performance (European Patent Application EP 288,907 to Squibb, published Nov. 2, 1988).

The AT2 selective antagonist PD123177 has been reported by Brix and Haberl (The FASEB Journal 6(4):A1264, 1992) to block the pial arterial dilation induced by angiotensin II in a rat cranial window preparation monitored by intravital microscopy. This suggests that PD123177 may have a role in modify cerebral blood flow.

The AT2 selective antagonist PD123177 also has been reported by Matsubara et al. (The FASEB Journal 6(4):A1859, 1992) to block the angiotensin II induced inhibition of trypsin activated collagenase in rat heart myocytes suggesting an effect in cardiac remodeling in cardiac failure.

The AT2 selective antagonist CGP42112A has been reported by LeNoble et al. (The FASEB Journal 6(4):A937, 1992) to block the increase in microvascular density induced by angiotensin II in the chick chorioallantoic membrane preparation suggesting a possible anti-angiogenesis effect of this class of compounds.

Evidence for a role of AII in cholinergic function was also reported by Barnes et al. (*Brain Research* 491:136–143 (1989)), who examined the effect of AII in an in vitro model of potassium stimulated release of [$^3$H]ACh. AII, but not AI, reduced potassium-stimulated release of ACh without effects on basal levels. This effect was antagonized by the AII antagonist [1-sarcosine, 8-threonine]angiotensin II. These results suggest that AII can inhibit the release of ACh in the entorhinal cortex of rat brain.

The results summarized above suggest that increased AII activity in the brain may exert an inhibitory effect on cholinergic neurons, resulting in impaired cognitive performance. Thus, compounds that block AII receptor activation may enhance cognitive performance.

Carini and Duncia, U.S. Ser. No. 050,341, filed May 22, 1987, which is a continuation-in-part of U.S. Ser. No. 884,920, filed Jul. 11, 1986, disclose angiotensin II receptor blocking imidazoles (also EP 0253 310, published 20.01.88, and EP 0324 377, published 19.07.89).

Blankley et al., U.S. Pat. No. 4,812,462, issued Mar. 14, 1989, to Warner-Lambert, disclose 4,5,6,7-tetrahydroimidazo-[4,5-c]-pyridine derivatives, which are said to be useful for the treatment of hypertension.

Ardecky et al., U.S. Pat. No. 5,091,390, issued Feb. 25, 1992, discloses 4,5,6,7-tetrahydro-1H-imidazo(4,5-c)-pyridines useful for treating disorders of mammals mediated by AII type-2 receptors in the central nervous system.

Takasugi et al., U.S. Pat. No. 5,059,608, issued Oct. 22, 1991, to Fujisawa, disclose a bicyclic amine compound and a process for the preparation thereof, useful as an anticonvulsant and for treatment of delayed neuronal death.

Anderson et al., EPO 0,401,676, published Dec. 12, 1990, to Bio-Mega, disclose enzyme inhibitors which are peptide derivatives useful in combating HIV infections or for treating hypertension or congestive heart failure. Structure 3 on page 6 is a tetrahydroisoquinoline, and is used as an intermediate in making the peptides of Anderson'patent publication.

SUMMARY OF THE INVENTION

According to the present invention, there are provided compounds of Formula I, pharmaceutical compositions containing them, and methods of using them to treat disorders mediated by AII receptors, including cognitive and learning disorders. Included are compounds of the formula:

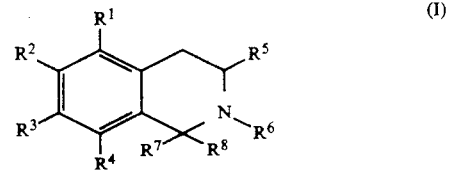

(I)

wherein $R^1$ and $R^2$ are independently hydrogen, alkyl of from 1 to 5 carbon atoms, cycloalkyl of from 3 to 7 carbon atoms, (CH2)m cycloalkyl where m is 1–4 and the cycloalkyl portion is of from 3 to 7 carbon atoms, —ORy, where Ry is H, alkyl of from 1 to 4 carbon atoms, phenyl or benzyl, perfluoroalkyl of from 3 to 7 carbon

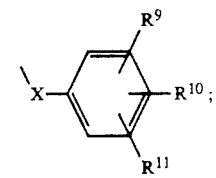

atoms, or $R^3$ and $R^4$ are independently hydrogen, alkoxy of from 1 to 5 carbon atoms, hydroxy, alkyl of from 1 to 5 carbon atoms, bromine, chlorine, or $S(O)_p$alkyl where p is 0–2 and the alkyl portion is of from 1 to 5 carbon atoms;

$R^5$ is —CO2R$^{12}$, —CH2OH, —CHO, —CONHOR$^{12}$, —NHSO2CF3,

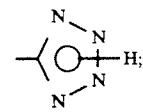

or $R^6$ is —COCHR$^{15}$R$^{16}$ or —CONR$^{14}$R$^{17}$;

$R^7$ and $R^8$ are independently hydrogen, or alkyl of from 1 to 5 carbon atoms;

$R^9$, $R^{10}$, and $R^{11}$ are independently hydrogen, alkyl of from 1 to 5 carbon atoms, phenyl, hydroxy, alkoxy of from 1 to 5 carbon atoms, —NO2, —NR$^{12}$R$^{13}$, —NR$^1$-2COR$^{13}$, fluorine, chlorine, bromine, iodine, —COR$^{14}$, —CF3, or —SR$^{12}$;

$R^{12}$ and $R^{13}$ are independently hydrogen, alkyl of from 1 to 5 carbon atoms, or phenyl;

$R^{14}$ is hydrogen, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO2, or —NR$^{12}$R$^{13}$;

$R^{15}$ and $R^{16}$ are independently cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO2, or —NR$^{12}$R$^{13}$;

$R^{17}$ is alkyl of from 1 to 5 carbon atoms, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO2, or —NR$^{12}$R$^{13}$;

X is —(CH$_2$)$_n$— where n is 0 to 5, —O—, —CO—, —S—, —(CH=CH)—, —NR$^{12}$CO—, —CONR$^{12}$—, —CH$_2$O—, —OCH$_2$—, —SCH$_2$—, or —CH2S—.

Preferred are compounds of Formula (I) above wherein

R$^1$ and R$^2$ are as above, except that R$^1$ and R$^2$ are not both hydrogen at the same time;

R$^3$ and R$^4$ are hydrogen;

R$^7$ and R$^8$ are hydrogen;

R$^{14}$ is cycloalkyl of from 3 to 7 carbon atoms, phenyl, or phenyl monosubstituted with alkyl of from 1 to 5 carbon atoms, hydroxy, alkoxy of from 1 to 4 carbon atoms, halogen, —CN, —NO$_2$, or —NR$^{12}$R$^{13}$.

Most preferred are the following compounds of Formula (I):

2-Diphenylacetyl-5-benzyl-1,2,3,4-tetrahydroisoquinoline-3-carboxylic acid.

2-Diphenylacetyl-5-phenyl-1,2,3,4-tetrahydroisoquinoline-3-carboxylic acid.

2-Diphenylacetyl-5-(p-methoxyphenyl)methyl-1,2,3,4-tetrahydroisoquinoline-3-carboxylic acid.

2-Diphenylacetyl-5-(p-methoxyphenyl)-1,2,3,4-tetrahydroisoquinoline-3-carboxylic acid.

2-(N-methyl-N-phenylcarbamoyl)-5-(p-methoxyphenyl)methyl-1,2,3,4-tetrahydroisoquinoline-3-carboxylic acid.

2-(N,N-Diphenylcarbamoyl)-5-(p-methoxyphenyl)-methyl-1,2,3,4-tetrahydroisoquinoline-3-carboxylic acid.

2-Diphenylacetyl-6-phenoxy-1,2,3,4-tetrahydroisoquinoline-3-carboxylic acid.

2-Diphenylacetyl-6-phenyl-1,2,3,4-tetrahydroisoquinoline-3-carboxylic acid.

2-Diphenylacetyl-5-pentyl-1,2,3,4-tetrahydroisoquinoline-3-carboxylic acid.

DETAILED DESCRIPTION OF THE INVENTION

The novel compounds of Formula (I) may be prepared using the reactions and techniques described in this section. The reactions are preformed in a solvent appropriate to the reagents and materials employed and suitable for the transformation being effected. It is understood by those skilled in the art of organic synthesis that the functionality present on the tetrahydroisoquinoline core and other parts of the molecule must be consistent with the chemical transformations proposed. This will frequently necessitate judgment as to the order of synthetic steps, protecting groups required, and deprotection conditions. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

Generally, compounds of formula (6) can be prepared from compounds of formula (1) in the manner described below and in Scheme 1. The benzyl alcohol is first converted to the mesylate (2) (where x=OMs), by reacting with methanesulfonyl chloride and triethylamine in dichloromethane. Alternatively, the benzyl alcohol could be converted to the benzyl halide (where X=Br, Cl) by reacting with con. HBr or con. HCl at reflux. The mesylate or the halide can then be displaced by the sodium or potassium salt of diethylformamidomalonate to give (3). The compound of formula (3) can then be dehydrated with phosphorus pentoxide, phosphorus oxychloride, or a combination of those two in a high boiling solvent such as toluene or xylene in a Bischler Naperalski type reaction to give (4). For examples see M. Whaley and T. R. Govindachaii, *Organic Reactions,* 6, 74, (1951). The imine (4) can then be reduced preferably with sodium cyanoborohydride in acetic acid to give the diester (5). The diester can be converted to the monoester (6) in a one pot reaction. First, both esters are completely hydrolyzed in an alcoholic solvent such as methanol or ethanol with an excess of base, usually 2 to 3 equivalents of potassium hydroxide or sodium hydroxide. In the same pot, the diacid is then decarboxylated by addition of an acid such as sulfuric acid at room temperature. Enough acid is then added to bring the solution to a pH of about 1. The reaction is then heated to reflux for 3 hours to convert the remaining carboxylic acid to its methyl ester.

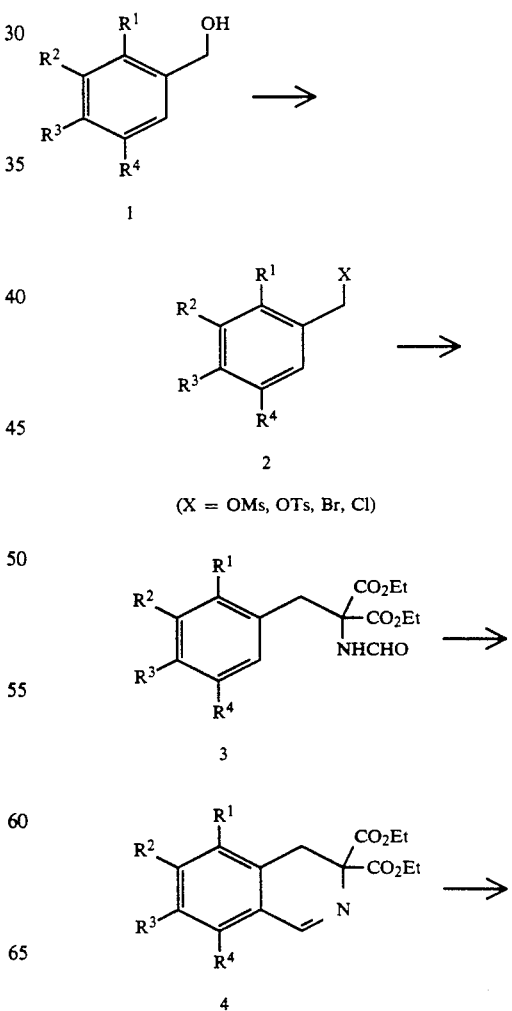

Scheme 1

-continued
Scheme 1

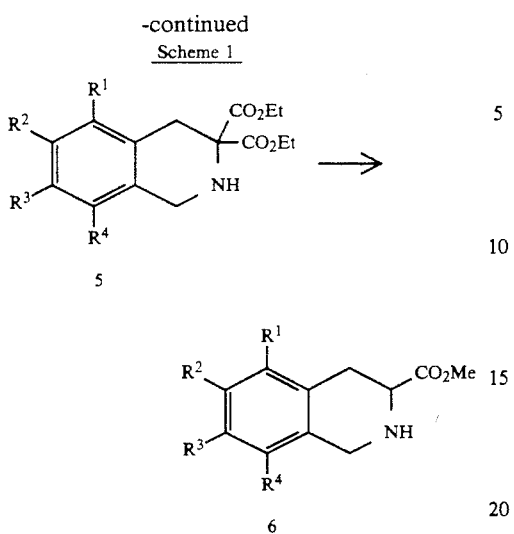

5

6

Compounds of formula (10) and (11) can be prepared starting with compounds of the formula (2) as is shown in Scheme 2. Diethyl aminomalonate is first reacted with the appropriate acid chloride in solvents such as ether, tetrahydrofuran (THF), or glyme in the presence of some tertiary amine such as triethylamine to give compounds of formula (7). Alternatively, diethyl aminomalonate could be converted to the amide using the appropriate carboxylic acid and dicyclohexylcarbodiimide. Compounds of formula (7) can then be converted to its sodium or potassium salt by reacting it in ethanol with sodium hydride or potassium hydride. The sodium or potassium salt can then be reacted with compounds of formula (2) to give a compound of formula (8). Compounds of formula (8) are converted to compounds of formula (9) which then can be converted to compounds of formula (10) (where $R^8=H$) by a sodium cyanoborohydride reduction. Compounds of formula (10) (where $R^8 \neq H$) can be formed by reacting (9) with one equivalent of the appropriate Grignard. For examples of this reaction, see Patai, "The Chemistry of the Carbon-Nitrogen Double Bond," pp. 266-272, Interscience, New York, 1970.

Scheme 2

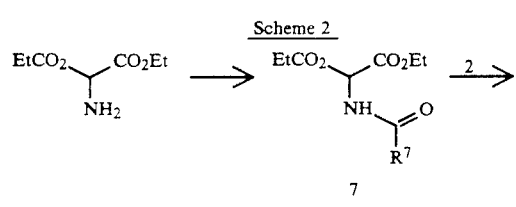

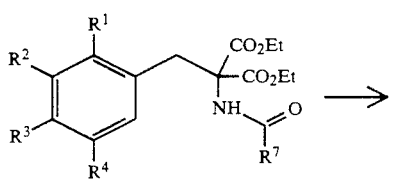

8

-continued
Scheme 2

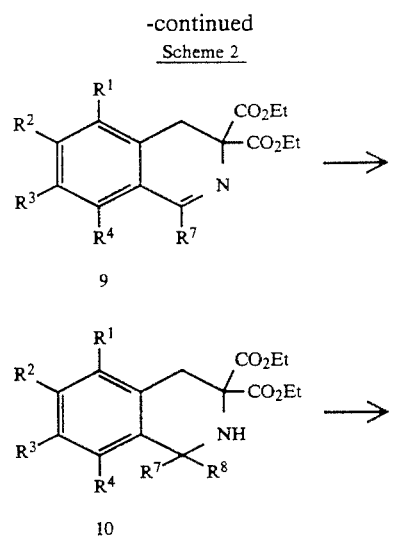

9

10

11

Compounds of formula (12) can be converted to their amides by reacting them with the appropriate acid chloride in an ethereal solvent such as ether, THF, or glyme in the presence of some tertiary amine such as triethylamine or diisopropylethylamine. Alternatively, the amine could be reacted with the appropriate carboxylic acid in the presence of dicyclohexylcarbodiimide.

Compounds of formula (14) can be formed by reacting (12) with the appropriate carbamoyl chloride in an ethereal solvent such as ether, THF or glyme in the presence of triethylamine or diisopropylethylamine. The carbamoyl chlorides that are not commercially available can be formed by reacting the amine with phosgene, see *J. Med. Chem* 10:541 (1967).

Compounds of formula (15) can be formed by reacting (12) with the appropriate alkyl halide (chloride, bromide or iodide), alkyl mesylate or tosylate. Alternatively, (12) could be reacted with the appropriately substituted acetaldehyde followed by reduction of the imine with sodium cyanoborohydride.

Scheme 3

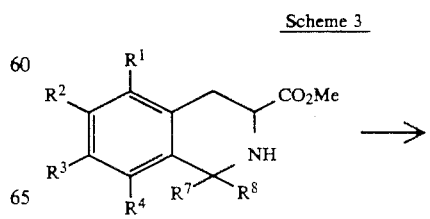

12

Compounds of formula (17), see Scheme 4, can be formed by hydrolyzing the corresponding ester using sodium hydroxide or potassium hydroxide in alcoholic solvents such as methanol or ethanol. Alternatively, the ester can be hydrolyzed by reacting it with an aqueous sodium or potassium hydroxide solution in THF. The ester can also be hydrolyzed under acidic conditions, such as 1 to 6 N HCl solution at room temperature to the reflux temperature of the solvent.

The level of oxidation at the C-6 position can be easily manipulated, see Scheme 5. The esters (16) can be reduced, using lithium borohydride in ether or THF as solvent, to the corresponding hydroxy methyl compound (18). The ester can also be reduced using sodium borohydride, in diglyme, and in the presence of lithium chloride. Compounds of formula (18) can then be oxidized to the aldehyde using pyridinium chlorochromate or pyridinium dichromate in dichloromethane. A solution of chromic acid and sulfuric acid in water (Jones reagent) will also convert the primary alcohol to the aldehyde. Alternatively, the alcohol can be converted using manganese dioxide in ether, THF, or dichloromethane. For an example, see "The Chemistry of Functional Groups, Supplemental E," pp. 469–538, Wiley, New York, 1980.

-continued
Scheme 5

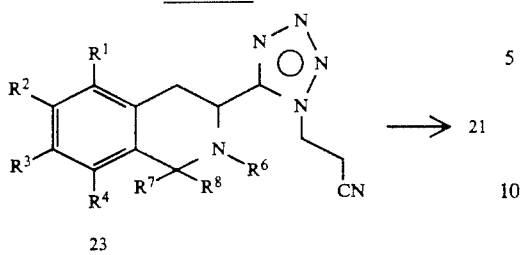

23

Scheme 6

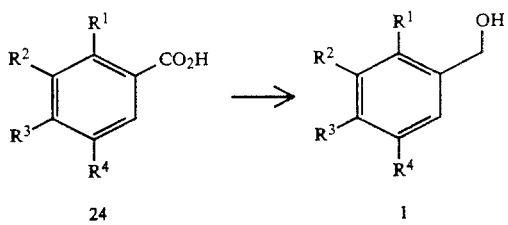

24  1

The hydroxamic acid (20) can be prepared by reacting the ester (16) with the appropriately substituted hydroxyl amine. Alternatively, the acid (17) can be converted to the acyl chloride by reacting with oxalyl chloride. The acid chloride can then be reacted with the appropriately substituted hydroxyl amine as is shown in Zabicky, "The Chemistry of Amides," pp. 731-857, Interscience, New York, 1970.

The tetrazole (21) can be prepared by starting with either the ester (16) or the acyl chloride and converting either one into the amide by reacting with ammonia. The amide can then be dehydrated to the nitrile by reaction with a dehydrating agent such as phosphorus oxychloride, trifluoroacetic anhydride and pyridine, or $SOCl_2$. For examples of amide formation, see Zabicky, "The Chemistry of Amides," pp. 274-283, Interscience, New York, 1970. The nitrile can then be converted to the tetrazole by reacting with sodium azide and ammonium chloride in dimethylformamide (DMF) at temperatures between 30° C. and reflux for 1-10 ten days, J. P. Hurwitz and A. J. Tomson, *J. Org. Chem.*, 26:3392 (1961). In the preferred method, the tetrazole is formed by reacting with tributyltin azide in xylene at reflux. An example of this method is shown in *J. Organometallic Chem.*, 337 (1971). The tetrazole can then be protected by reacting with trityl chloride. The protected tetrazole can then be purified by chromatography and subsequently deprotected using a dilute acid solution or methanol. The tetrazole (21) can also be formed by reacting the carboxylic acid (17) with thionyl chloride to give the acid chloride. The acid chloride can then be reacted with 2-aminoproprionitrile to give the amide (22). The amide can then be reacted with triphenylphosphine, diethylazodicarboxylate, and trimethylsilylazide in THF to give the protected tetrazole (23). The protected tetrazole can then be stirred in 1 N sodium hydroxide, then acidified to yield the deprotected tetrazole, for this procedure, see J. V. Duncia, M. E. Pierce, J. B. Santella, *J. Org. Chem.*, 56:2395 (1991).

A large number of ortho-substituted benzyl alcohols are commercially available. Some that are not available as the benzyl alcohol are available as the carboxylic acid. The benzoic acids (24) can be reduced to the benzyl alcohols be reaction with borane in THF or ether (see Scheme 6). Alternatively, the acids can first be converted into their esters by refluxing in methanol with a catalytic amount of acid. The esters can then be reduced using lithium borohydride in ether. The esters can also be reduced using lithium aluminum hydride in ether.

The ortho-alkyl benzoic acids can be made by using Meyer's chemistry, A. I. Meyers and E. D. Mihelich, *J. Am. Chem. Soc.*, 97:7383 (1975), see Scheme 7. The Grignard of the appropriate alkyl halide, cylcoalkyl halide, or alkylcycloalkyl halide can be added to o-methoxyphenyloxazoline (25). The oxazoline can then be hydrolyzed in refluxing 1 to 6 N HCl to give the substituted carboxylic acid.

The ortho-phenyl benzoic acids can be made in the same manner as the otho-alkyl benzoic acids. The Grignard reagent of a substituted phenyl bromide can be added to o-methoxyphenyloxazoline (25).

Scheme 7

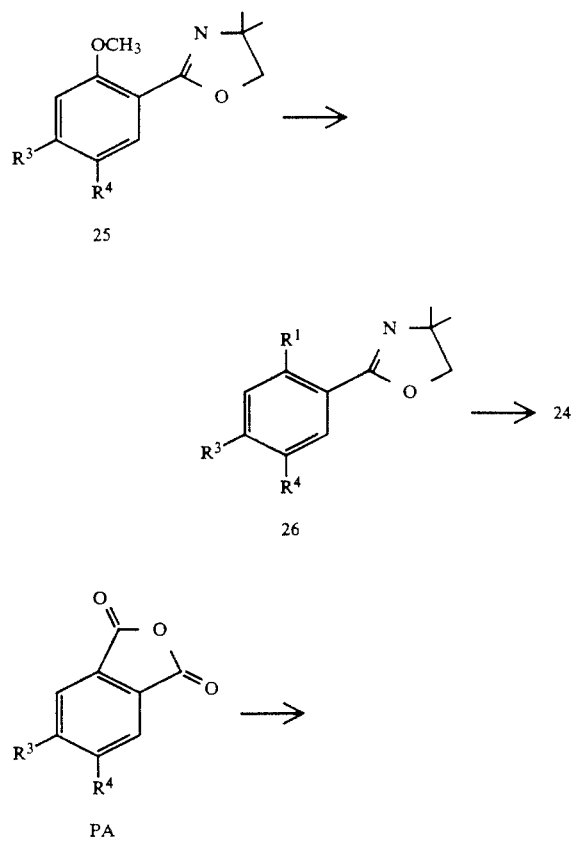

Scheme 7

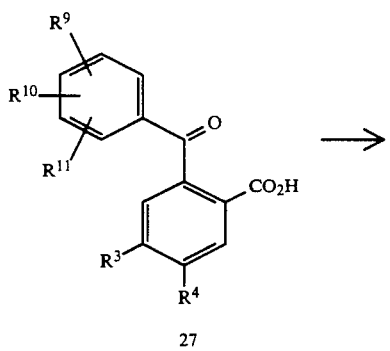
27

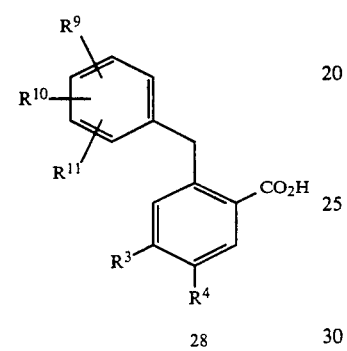
28

The compounds of formula (28) can be prepared by reacting the Grignard reagent of the appropriately substituted phenyl halide with phthalic anhydride (PA) to give compounds of formula (27). The ketone can then be reduced using high hydrogen pressures at elevated temperatures, for example, 20 atmospheres of hydrogen, 70° C., in an alcoholic solvent to give the orthosubstituted benzoic acid (28). This series of reactions is illustrated in J. Fouche et al., *Bull. Soc. Chim. Fr.*, 8:3113 (1972).

The compounds of formula (30) can be prepared by the coupling reaction of the o-hydroxy benzoate (29) with an appropriately substituted aryl halide using the Ullman copper coupling procedure, described in "Organic Reactions," 2:6 (1944), see Scheme 8. The ester can then reduced to the hydroxy methyl compound (31) using methods described earlier. The compounds of formula (29) can also be benzylated. The appropriate benzyl halide can be coupled with the phenol (29) by using potassium carbonate in a solvent such as acetone or DMF.

-continued
Scheme 8

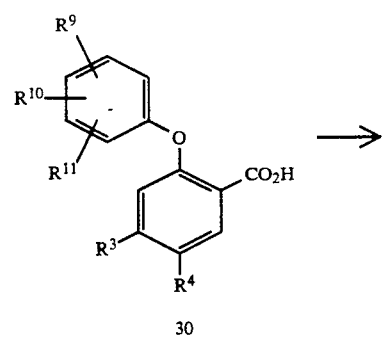
30

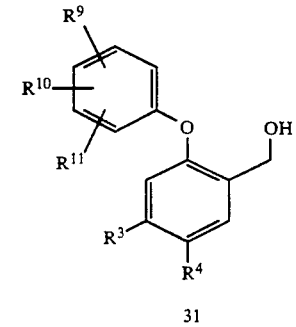
31

29 →

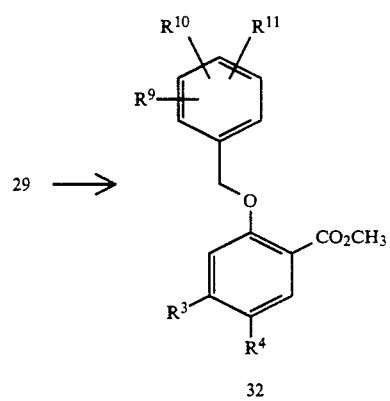
32

The diaryl sulfide (34) can be made by reacting the thiol compound (33) with an aryl bromide in an inert solvent such as DMF or DMSO, see "The Chemistry of the Thiol Group," pt. 2, pp. 735-744, Wiley, New York, 1974, see Scheme 9. If the thiol compound (33) is reacted with a benzyl bromide and potassium carbonate in an inert solvent such as acetone or DMF, the benzylated compound (35) can be obtained.

Scheme 8

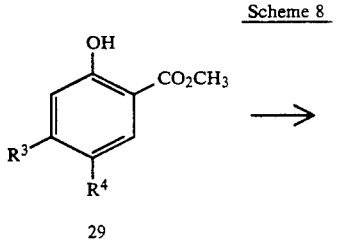
29

Scheme 9

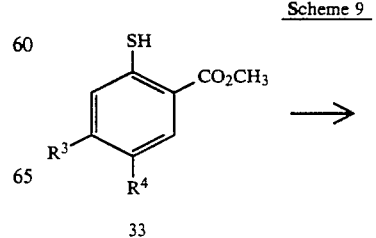
33

Scheme 9

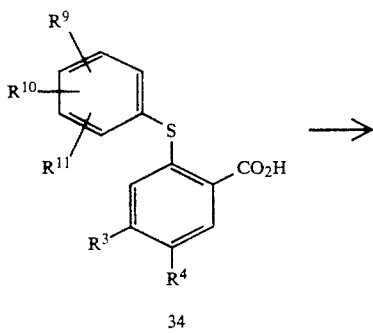

34

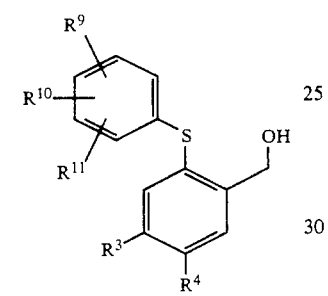

33 →

35 o-Amino benzoate (36) can be reacted with an appropriate benzoyl chloride to give the amide (37), as is illustrated in Scheme 10. This reaction can be performed under standard conditions such as those described earlier. The amide can also be formed by reacting the amine and acid together in the presence of dicyclohexylcarbodiimide in acetonitrile or dichloromethane.

Scheme 10

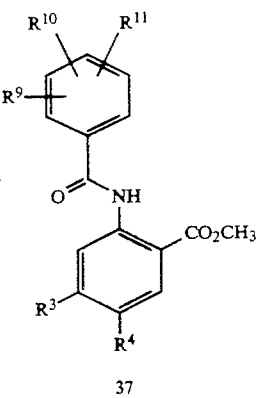

Phthalic anhydride can be reacted with the appropriately substituted aniline to give the phthalamic acid (38). This reaction can be run in either, THF, or dichloromethane at temperatures anywhere from room temperature up to the reflux temperature of the solvent. Examples of these types of reactions are shown in M. L. Sherrill et al. *J. Am. Chem. Soc.*, 50:474 (1982).

Scheme 11

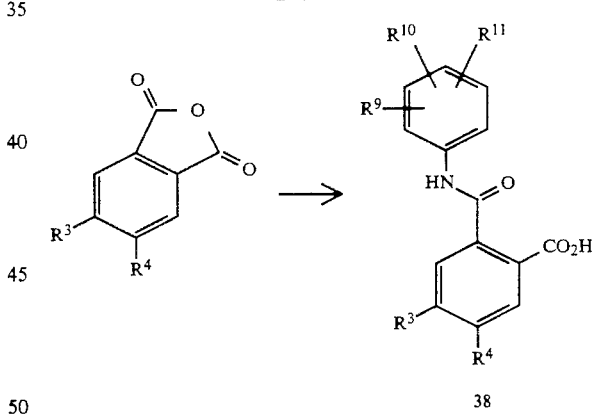

38

Compounds of formula (39) and (40) can be obtained by reacting the appropriate nucleophile with the monomesylate of o-xylene alpha,alpha diol. The monomesylate of the diol can be prepared by carefully controlling the proportions of starting materials. The appropriate nucleophiles in this case are the anion of phenol, which can be generated from the phenol and NaH, in a solvent such as THF or ether, or the anion of thiophenol which can be generated in a similar manner. The different isomers can then be separated from each other using standard methods.

Scheme 12

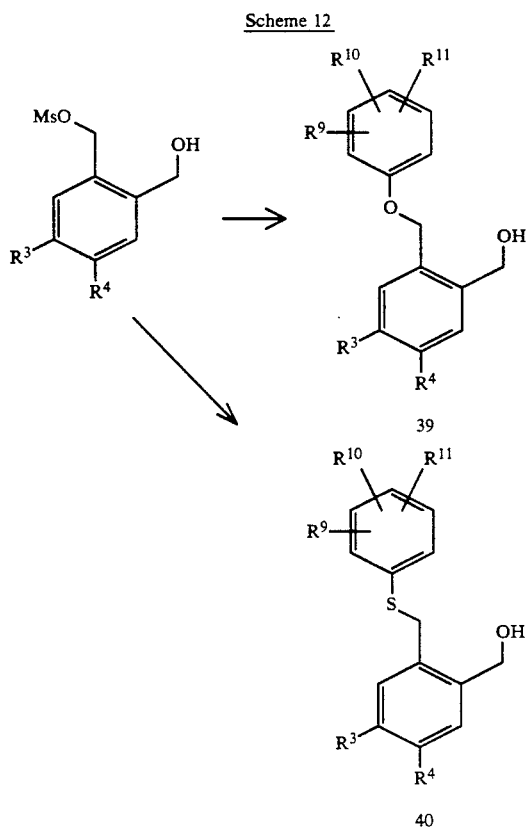

Several meta-substituted benzyl alcohols and carboxylic acids are available commercially. These m-substituted benzyle alcohols give rise to substituents at the 6-position of the tetrahydroisoquinoline ring system. Other types of substituents which are not commercially available can be prepared as described below. The first method begins with m-iodobenzyl alcohol (41). This benzyl alcohol can be converted to the tetrahydroisoquinoline carboxylic acid using the same reaction sequence that was shown in Scheme 1. The free amine can then be acylated or alkylated as was demonstrated in Scheme 3. The aryl iodide on the compound of formula (42) can then be coupled to an aryl boronic acid using the a palladium coupling (Suzuki Reaction) to give compounds of the general formula (43), see M. J. Sharp and V. Snieckus, *Tett. Lett.*, 26:5997 (1985). Alkyl groups can be introduced via a palladium catalyzed coupling to an alkyne, followed by hydrogenation of the double bond.

Scheme 13

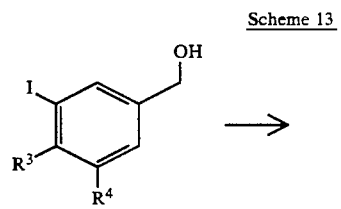

-continued
Scheme 13

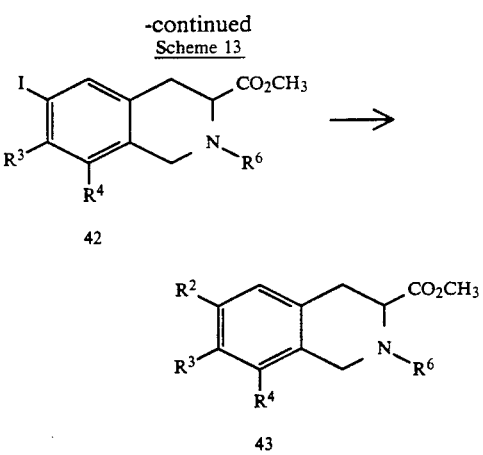

Compounds of formula (48) can be made by the method shown in Scheme 14. m-Tyrosine can cyclized under Pictet Spengler conditions, see P. L. Ornstein et al., *J. Org. Chem.*, 56:4388 (1991), in a weakly acidic solution at 95° C. for 45 minutes. The ester can then be formed by placing it in methanol and bubbling HCl gas through for 20 minutes. The reaction is then heated to reflux for 12 hours. The amine can be protected as the tBOC. The phenol can then be substituted with various alkyl and aryl groups. Alkyl groups can be added by reacting (46) with an alky halide (preferably iodide) in the presence of potassium carbonate in an inert solvent such as acetone or DMF. Aryl groups can be introduced in the same manner as was shown in Scheme 8. The tBOC group can then be removed under weakly acidic conditions, such as a small amount of mineral acid in alcoholic solvent or in trifluoroacetic acid.

Compounds of formula (46) can also be converted to their triflate. These triflates can be formed under a variety of conditions. One example is pyridine and triflic anhydride. The triflates of compounds (46) can then be converted to alkyl or aryl groups at the 6-position by doing a palladium coupling to an organotin compound. This series of reactions is illustrated in A. M. Echavarren and J. K. Stille, *J. Am. Chem. Soc.*, 109:5478 (1987).

Scheme 14

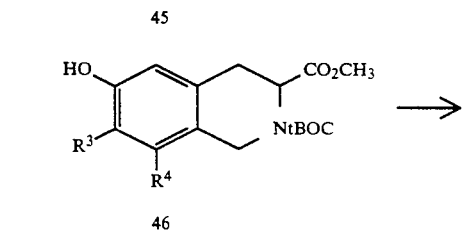

-continued
Scheme 14

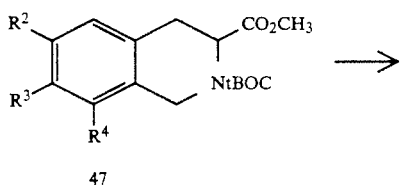

47

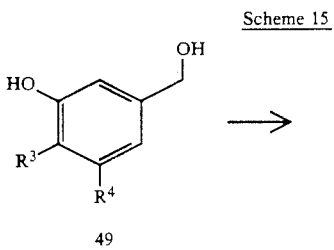

48

Compounds of formula (50) can also be made by starting with the m-hydroxybenzyl alcohol, see Scheme 15. This benzyl alcohol can be converted to the tetrahydroisoquinoline carboxylic acid using the same method as described in Scheme 1 to give the compound of formula (50). This compound can then be converted to in the same manner as was shown in Scheme 14.

Scheme 15

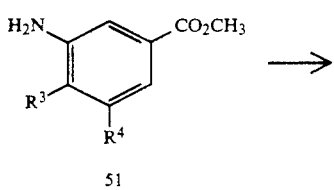

49

50

Compounds of formula (51) can be acylated with substituted benzoyl chlorides to give compounds of formula (52) Alternatively, the compound could be reacted with a carboxylic acid in the presence of dicyclohexyl carbodiimide. The ester can then be reduced to the benzyl alcohol which can then be further elaborated to compounds of formula (17) with the tetrahydroisoquinoline core structure using the procedure outlined in Scheme 1.

Scheme 16

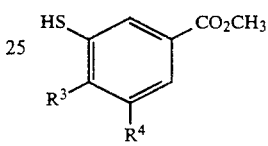

51

-continued
Scheme 16

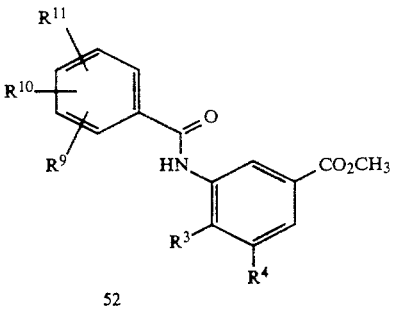

52

Compounds of formula (53) can be arylated in a manner similar to Scheme 9 to give compounds of formula (54). Compounds (53) can also be benzylated in the same manner as described before to give compounds (55), see Scheme 17.

Scheme 17

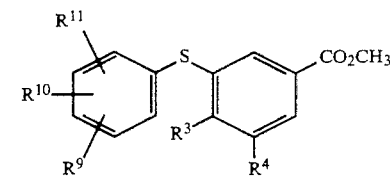

53

$53 \longrightarrow$

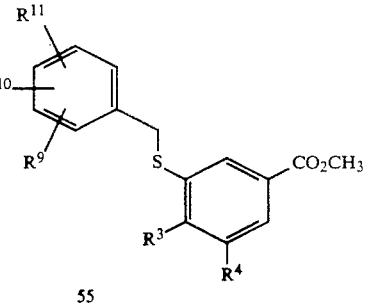

54

55

The carboxylic acid (17) can be converted to the acyl azide compound (56) by first converting to the acid chloride, which was described in Scheme 5. The acyl azide is then formed by trapping with azide ion, for a review, see Patai, "The Chemistry of the Azido Group," pp. 57–119, Interscience, New York, 1971. The acyl azide (56) can then undergo a Curtius type reaction to give the primary amine (57), for an example of this reaction, see J. R. Pfister and W. E. Wymann, Synthesis, 38, (1983). This primary amine can then be trapped using either methanesulfonyl chloride, trifluoromethanesulfonyl chloride or trifluormethanesulfonyl anhydride, using standard conditions, such as dichloromethane and triethylamine, to give compounds of formula (58) and (59).

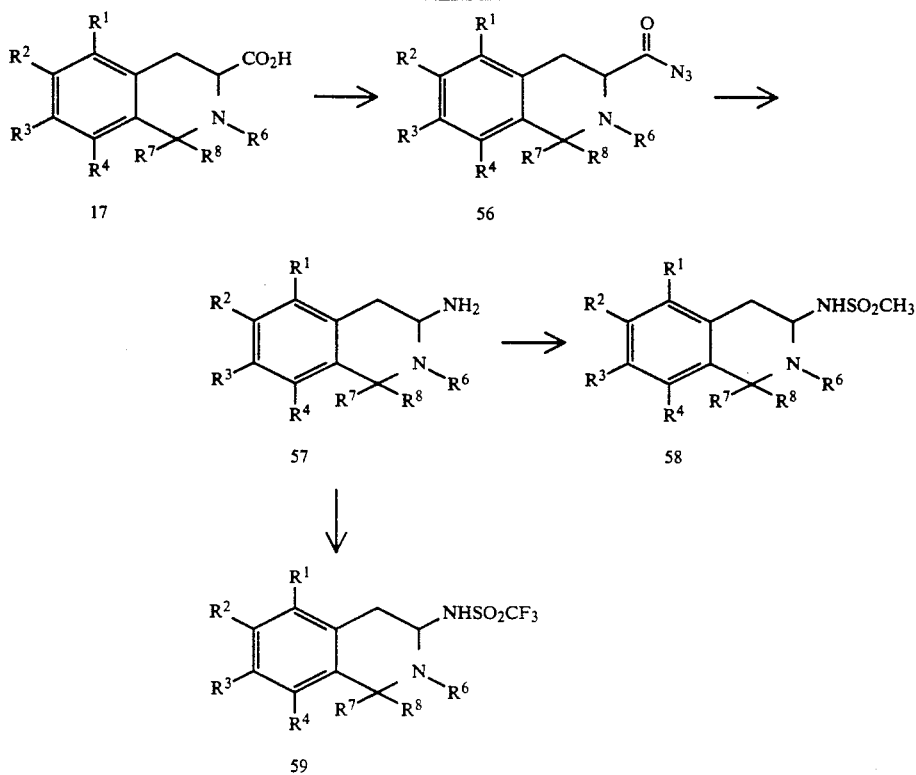

Scheme 18

The compounds of this invention and their preparation can be understood further by the following examples, which do not constitute a limitation of the invention.

EXAMPLES

Example 1

Methyl 2-diphenylacetyl-5-phenyl-1,2,3,4-tetrahydroisoquinoline-3-carboxylate

A solution of biphenylmethyl alcohol (6.07g, 33.0 mmoles) and triethylamine (9.2 mls, 66 mmoles) in 125 ml of dichloromethane was dripped into an ice bath-cooled solution of methanesulfonyl chloride (5.1 mls, 66 mmoles) in 150 ml of dichloromethane. After 1 hour, the solution was washed with 10% sodium bicarbonate solution, dried over MgSO$_4$, and evaporated to give the crude product.

NaH (1.02 g, 34.0 mmoles) was carefully added to 200 ml of ethanol. Diethylformamidomalonate (6.92 g, 34.1 mmoles) was then added. After 5 minutes, the crude mesylate was added. The reaction then stirred at room temperature overnight. The solvent was evaporated. The residue was taken up in dichloromethane, washed with 1.0 N NaOH solution, dried over MgSO$_4$ and evaporated to give an oil (9.65 g, 26.2 mmoles) which solidified on standing.

The malonate derivative was place in 300 ml of toluene P$_2$O$_5$ (~10 g) was added. The reaction was heated to reflux for 4 hours. After cooling, the reaction was carefully quenched with water. The water layer was made basic, then separated. It was then extracted twice with dichloromethane. The combined toluene and dichloromethane extracts were dried over MgSO$_4$ and evaporated to give product (8.18 g, 23.3 mmoles) as a brown oil.

The cyclized product was placed in 100 ml of glacial acetic acid. NaCNBH$_3$ (8.18 g, 23.3 mmoles) was slowly added. The reaction was stirred at room temperature for 15 minutes. The reaction was diluted with water and then quenched carefully with conc. NaOH then extracted with dichloromethane. The combined extracts were dried over MgSO$_4$ and evaporated to give crude ethyl-5-phenyltetrahydroisoquinoline-3,3-dicarboxylate.

The crude diester was placed in 300 ml of methanol. Approximately 2 equivalents of KOH (4.94g, 88.2 mmoles) was added. The reaction was heated to reflux for 4 hours. After cooling, conc. sulfuric acid (15 mls) was carefully added. The reaction was heated to reflux for 4 more hours. The solvent was evaporated. The residue was taken up in water, neutralized with 10% K$_2$CO$_3$, and extracted with dichloromethane. The extracts were dried over MgSO$_4$ and evaporated to give methyl-5-phenyltetrahydroisoquinoline-3-carboxylate (6.45 g, 22.8 mmoles) as a yellow oil.

The methyl ester was placed in 300 mls of dry THF. Diisopropylethylamine (2.9mls, 23 mmoles) was added. After 5 minutes, diphenylacetylchloride (5.30 g, 23.0 mmoles) was added. The reaction was stirred at room temperature overnight. The solvent was evaporated. The residue was taken up in dichloromethane, washed with water, dried over MgSO$_4$, and evaporated. Product was then purified by column chromatography (1% methanol/dichloromethane) and subsequently with HPLC to give a solid, m. p. 149°–150° C.

Examples 2–5 in Table 1 may be prepared by the procedure described in Example 1, using the appropriate reactants.

TABLE 1

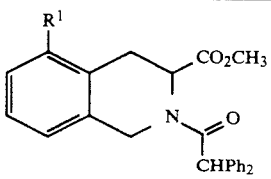

| Example # | R¹ | m.p. (°C.) |
|---|---|---|
| 1 | phenyl | 149–150 |
| 2 | benzyl | 139–141 |
| 3 | methyl | 137–138 |
| 4 | ethyl | — |
| 5 | —CF₃ | — |

Example 6

2-Diphenylacetyl-5-phenyl-1,2,3,4-tetrahydroisoquinoline-3-carboxylic acid

The above methyl ester, Example 1, (0.60 g, 13 mmoles) was placed in 20 ml of methanol and 7 mls of THF. 1.0 N NaOH (2.0 mls) was added and the reaction was heated to reflux for 4 hours. The solvent was evaporated. The residue was taken up in water and extracted with ether. The aqueous was acidified and extracted with ether. The acidic ether extracts were dried and evaporated to give the solid product (0.55 g, 1.2 mmoles), m.p. 216°-221° C.

Examples 7-10 in Table 2 may be prepared by the procedure described in Example 6, using the appropriate reactants.

TABLE 2

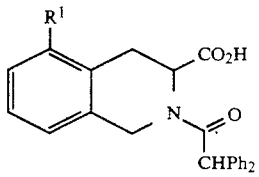

| Example # | R¹ | m.p. (°C.) |
|---|---|---|
| 6 | phenyl | 216–221 |
| 7 | benzyl | 95–100 |
| 8 | methyl | 85–95 |
| 9 | ethyl | — |
| 10 | —CF₃ | — |

Example 11

2-Diphenylacetyl-5-(p-methoxyphenyl)methyl-1,2,3,4-tetrahydroisoquinoline-3-carboxylic acid

Part A: Preparation Of P-(methoxyphenyl)methylbenzyl Alcohol.

Freshly cleaned magnesium ribbon (1.6 g) was placed in 150 ml of ether. p-Bromoanisole (7.5ml, 60 mmoles) was added. Iodine and 1,2-dibromoethane was added to initiated and the reaction was heated to reflux for one hour. Phthalic anhydride (8.79 g, 59.4 mmoles) was place in 50 ml of ether and 90 ml of benzene. The grignard solution was then transferred slowly into the phthalic anhydride solution. The reaction was then heated to reflux overnight. The reaction was carefully quenched with sat. NH₄Cl solution. It was then extracted three times with ether, dried over MgSO₄, and evaporated to give a yellow foam (10.71 g, 41.8 mmoles) in 70% yield.

The above keto-acid was placed in 50 ml of methanol along with 5% palladium on carbon (2.48 g). The solution was place under 20 atmospheres of hydrogen, at 70° C., for 12 hours. The reaction was filtered through celite. The celite was washed well with methanol. The combined methanol was evaporated to give a the o-benzylbenzoic acid as a white solid (8.09 g, 33.4 mmoles) in 85% yield.

The above benzoic acid was place in 250 ml of methanol. Conc. H2SO₄ (5 ml) was added. The reaction was heated to reflux for 4 hours. The solvent was evaporated. The residue was placed in water and extracted three times with dichloromethane. The combined organic extracts were dried over MgSO₄ and evaporated to give the benzoic ester as an oil (8.37 g, 33.4 mmoles) in 98% yield.

The benzoic ester was placed in 250 ml of ether. An excess of LiBH₄ (2.95 g, 134 mmoles) was added. The reaction was stirred at room temperature overnight. The ether was evaporated. Methanol was carefully added to destroy the LiBH₄. The reaction was then diluted with water and extracted with dichloromethane. The combined dichloromethane extracts were dried over MgSO₄ and evaporated to give the benzyl alcohol in 84% yield (6.28 g, 27.5 mmoles).

Part B

The p-substituted benzyl alcohol was then converted to the tetrahydroisoquinoline in a similar manner as was illustrated in Examples 1 and 6.

Examples 12-18 in Tables 3 and 4 may be prepared by the procedure described in Example 11, using the appropriate reactants.

TABLE 3

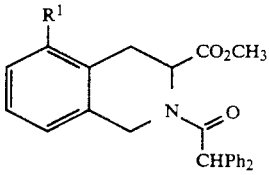

| Example # | R¹ | m.p. (°C.) |
|---|---|---|
| 11 | (p-methoxyphenyl)methyl | 54–60 |
| 12 | (4-methoxy-3-methylphenyl)methyl | — |
| 13 | (3,4-dimethoxyphenyl)methyl | — |
| 14 | (p-methylphenyl)methyl | — |

TABLE 4

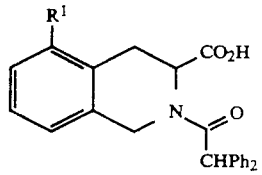

| Example # | R¹ | m.p. (°C.) |
|---|---|---|
| 15 | (p-methoxyphenyl)methyl | 85–90 |
| 16 | (4-methoxy-3-methylphenyl)methyl | 78–88 |
| 17 | (3,4-dimethoxyphenyl)methyl | — |
| 18 | (p-methylphenyl)methyl | — |

EXAMPLE 19

2-Diphenylacetyl-5-(p-methoxyphenyl)-1,2,3,4-tetrahydroisoquinoline-3-carboxylic acid

Part A

A THF solution of p-bromoanisole was prepared in a similar manner as was described in Example 11. The grignard solution was then carefully added to a solution of o-methoxyphenyloxazoline (6.16g, 30 mmoles) in 50 ml of THF. The reaction was stirred at room temperature overnight. The reaction was quenched with sat. $NH_4Cl$ solution. The solution was extracted with ethyl actated. The combined organic extracts were dried over $MgSO_4$ and evaporated. The material was then chromatographed using 25–50% ethyl acetate in pentane to give product (6.65 g, 23.7 mmoles) in 79% yield.

The above product was placed in 150 ml of 4.5 N HCl. The reaction was heated to reflux overnight. The reaction was extracted three times with ether. The combined ether was dried over $MgSO_4$ and evaporated to give the benzoic acid as a white solid (4.08 g, 17.9 mmoles) in 75% yield.

This substituted benzoic acid can be converted to the benzyl alcohol as was described in Example 11 and can then be converted to the tetrahydroisoquinoline as was described in Example 1.

Examples 20–23 in Table 5 may be prepared by the procedure described in Examples 1, 6 and 11, using the appropriate reactants.

TABLE 5

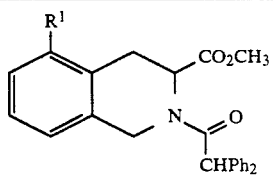

| Example # | $R^1$ | m.p. (°C.) |
|---|---|---|
| 19 | p-methoxyphenyl | 61–63 |
| 20 | 4-methoxy-3-methylphenyl | — |
| 21 | propyl | — |
| 22 | butyl | — |
| 23 | pentyl | — |

Part B

The esters of Table 6 can then be hydrolized to the carboxylic acid as was described in Example 6, to give the acids of Table 6.

TABLE 6

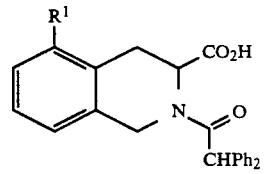

| Example # | $R^1$ | m.p. (°C.) |
|---|---|---|
| 24 | p-methoxyphenyl | 90–97 |
| 25 | 4-methoxy-3-methylphenyl | 100–110 |
| 26 | propyl | — |
| 27 | butyl | — |
| 28 | pentyl | 45–50 |

Example 32

2-Diphenylacetyl-6-phenoxy-1,2,3,4-tetrahydroisoquinoline-3-carboxylic acid

Part A m-Phenoxybenzyl alcohol can be converted to the corresponding tetrahydroisoquinoline carboxylic ester in a similar manner as was described in Example 1.

TABLE 7

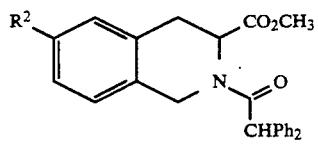

| Example # | $R^2$ | m.p. (°C.) |
|---|---|---|
| 29 | phenoxy | (a) |
| 30 | methoxy | — |
| 31 | ethoxy | — |

(a) NMR data $(CDCl_3)$-2x amide isomers, 7.4–6.8 (m, 18H), 5.57 & 5.45 (m, 1H), 5.37 (s, 1H), 4.75 (d, J=16, 1H), 4.54 (d, J=16, 1H), 3.64 (s, 3H), 3.2–3.0 (m, 2H).

Part B

The ester can be hydrolyzed to the carboxylic acid in a similar manner as was described in Example 6.

TABLE 8

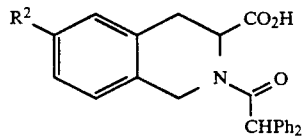

| Example # | $R^2$ | m.p. (°C.) |
|---|---|---|
| 32 | phenoxy | 81–88 |
| 33 | methoxy | — |
| 34 | ethoxy | — |

Example 35

2-Diphenylacetyl-6-phenyl-1,2,3,4-tetrahydroisoquinoline-3-carboxylic acid

Part A m-Tyrosine (12.59 g, 70.0 mmoles) was placed in 100 ml of 0.05 N HCl. Aqueous formaldehyde (9.6 ml) was added. The reaction was heated to 95° C. for 45 minutes. After cooling, the solids were filtered. The solids were washed twice with 40 ml of water and twice with 40 ml of acetone. The solids were then dried to give product as a white solid (12.54 g, 65.0 mmoles) in 93% yield.

The above product was place in 200 ml of methanol. HCl gas was bubbled through the solution for 20 minutes. The reaction was then heated to reflux overnight. The solvent was evaporated to give the methyl ester as a white solid (12.90 g, 53.98 mmoles) in 82% yield.

The methyl ester (1.03 g, 4.23 mmoles) was placed in 100 ml of glyme. Diisopropylethylamine (1.5 ml, 8.4 mmoles) was added. After 5 minutes, diphenylacetyl chloride (1.03 g, 4.47 mmoles) was added. The reaction was stirred at room temperature overnight. The solvent was evaporated. The residue was placed in dichloromethane, washed with water, dried over $MgSO_4$ and evaporated. The material was chromatographed using 5% methanol in dichloromethane to give product as a white solid (0.42g, 1.0 mmoles) in 25% yield.

The above product was placed in 5 ml of pyridine. The solution was cooled in an ice bath. Trifluoromethanesulfonic anhydride (0.34 ml, 2.0 mmoles) was dripped into the solution. The reaction stirred at 0° C. for 5 minutes. It was then warmed to room temperature and left overnight. The reaction was poured into 25 ml of water and extracted three times with ether. The combined ether extracts were washed with water, 10% HCl, water, and brine, then dried over MgSO4 and evaporated. The triflate was obtained as a white solid (0.49 g, 0.92 mmoles) in 90% yield.

LiCl (0.11 g, 2.6 mmoles), phenyltrimethyltin (0.24 g, 1.0 mmoles), and the above triflate were place in 15 ml of dioxane. Tetrakistriphenylphosphinepalladium (0) (0.11 g, 0.095 mmoles) was then added. The reaction was heated to reflux for 3 days. The reaction was poured into butyl chloride and was washed twice with water. The butyl chloride was evaporated. The residue was chromatographed using 50% ethyl acetate in hexane. Methyl 2-Diphenylacetyl-6-phenyltetrahydroisoquinoline-3-carboxylate was obtained as a foam (0.19 g, 0.41 mmoles) in 45% yield.

TABLE 9

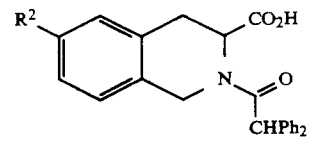

| Example # | R² | m.p. (°C.) |
|---|---|---|
| 35 | phenyl | (b) |
| 36 | p-methoxyphenyl | — |
| 37 | 4-methoxy-3-methylphenyl | — |
| 38 | 3,4-dimethoxyphenyl | — |

(b) NMR (CDCl₃)-2 amide isomers, 7.5–7.0 (m, 18H), 5.57 & 4.98 (2xm, 1H), 5.39 & 5.20 (2xs, 1H), 4.80 (d, J=15, 1H), 4.62 (d, J=15, 1H), 3.62 & 3.52 (2xs, 3H), 3.4–3.2 (m, 2H).

Part B

2-Diphenylacetyl-6-phenyltetrahydroisoquinoline-3-carboxylic acid can then be obtained by hydrolyzing the ester as was described in Example 6.

TABLE 10

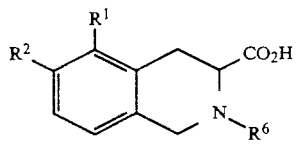

| Example # | R² | m.p. (°C.) |
|---|---|---|
| 39 | phenyl | 93–103 |
| 40 | p-methoxyphenyl | — |
| 41 | 4-methoxy-3-methylphenyl | — |
| 42 | 3,4-dimethoxyphenyl | — |

EXAMPLE 51

2-N,N-Diphenylurea-5-(p-methoxyphenyl)methy-1,2,3,4-tetra-hydroisoquinoline-3-carboxylate acid Methyl 5-(p-methoxyphenyl)methyltetrahydroisoquinoline-3-carboxylate (0.95 g, 3.1 mmoles) and diisopropyl-ethylamine (0.53 ml, 3.0 mmoles) was placed in 200 ml of THF. After 5 minutes, diphenylcarbamoyl chloride (0.72 g, 3.1 mmoles) was added. The reaction stirred at room temperature overnight. The solvent was evaporated. The residue was taken up in dichloromethane, washed with water, dried over MgSO4 and evaporated. The product was then chromatographed using 0–2% methanol in dichloromethane to give an amorphous solid (0.57 g, 1.1 mmoles) in 36% yield.

The ester was hydrolyzed to the carboxylic acid, m.p. 77°–85° C., using the procedure shown in Example 6.

In a similar manner, the following compounds in Table 11 below can be made.

TABLE 11

| Example # | R¹ | R² | R⁶ | m.p. |
|---|---|---|---|---|
| 43 | benzyl | H | —COH(Ph)₂ | — |
| 44 | benzyl | H | —CON(CH₃)Ph | — |
| 45 | benzyl | H | —CON(pentyl)₂ | — |
| 46 | benzyl | H | —CON(cyclohexyl)₂ | — |
| 47 | phenyl | H | —CONPh₂ | |
| 48 | phenyl | H | —CON(CH₃)Ph | |
| 49 | phenyl | H | —CON(pentyl)₂ | |
| 50 | phenyl | H | —CON(cyclohexyl)₂ | |
| 51 | (p-methoxyphenyl)methyl | H | —CONPh₂ | 77–85 |
| 52 | " | H | —CON(CH₃)Ph | (c) |
| 53 | " | H | —CON(pentyl)₂ | |
| 54 | " | H | —CON(cyclohexyl)₂ | |
| 55 | p-methoxyphenyl | H | —CONPh₂ | |
| 56 | " | H | —CON(CH₃)Ph | |
| 57 | " | H | —CON(pentyl)₂ | |
| 58 | " | H | —CON(cyclohexyl)₂ | |
| 59 | H | phenoxy | —CONPh₂ | |
| 60 | H | " | —CON(CH₃)Ph | 65–75 |
| 61 | H | " | —CON(pentyl)₂ | |
| 62 | H | " | —CON(cyclohexyl)₂ | |
| 63 | H | phenyl | —CONPh₂ | |
| 64 | H | " | —CON(CH₃)Ph | |

TABLE 11-continued

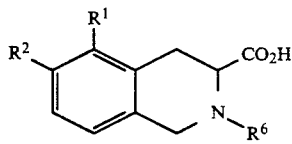

| Example # | $R^1$ | $R^2$ | $R^6$ | m.p. |
|---|---|---|---|---|
| 65 | H | " | —CON(pentyl)$_2$ | |
| 66 | H | " | —CON(cyclohexyl)$_2$ | |

(c) NMR (acetone) 7.2–6.8 (m, 12H), 4.86 (dd, J=5,6, 1H), 4.32 (d, J=16, 1H), 4.14 (d, J=16, 1H), 3.92 (s, 2H), 3.76 (s, 3H), 3.19 (s, 3H), 2.81 (m, 1H), 3.16 (m, 1H).

Example 67

2-Diphenylacetyl-3-hydroxymethyl-5-(p-methoxyphenyl)-1,2,3,4,-tetrahydroisoquinoline Methyl 2-Diphenylacetyl-5-(p-methoxyphenyl)1,2,3,4-tetrahydroisoquinoline-3-carboxylate (0.47 g, 0.93 mmoles) was placed in 50 ml of ether. LiBH$_4$ (0.10 g, 4.5 mmoles) was added. The reaction was stirred at room temperature for 3 days. The ether was evaporated. Methanol was carefully added to quench the LiBH$_4$. The solution was diluted with water and then extracted with dichloromethane. The extracts were dried over MgSO$_4$ and evaporated. The material was then chromatographed using 0–4% methanol in dichloromethane to give product (0.16 g, 0.33 mmoles) in 35% yield, m.p. 57°–63° C.

In a similar manner, the following compounds of Table 12 below can be made.

TABLE 12

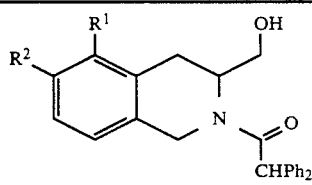

| Example # | $R^1$ | $R^2$ | m.p. |
|---|---|---|---|
| 67 | (p-methoxyphenyl)methyl | H | 57–63 |
| 68 | (4-methoxy-3-methylphenyl)methyl | H | — |
| 69 | p-methoxyphenyl | H | — |
| 70 | 4-methoxy-3-methylphenyl | H | |
| 71 | phenyl | H | |
| 72 | benzyl | H | |
| 73 | H | phenoxy | |
| 74 | H | phenyl | |
| 75 | H | p-methoxyphenyl | |
| 76 | H | 4-methoxy-3-methylphenyl | |

Utility

We have found and characterized two distinct angiotension II (AII) receptor subtypes by means of the discriminatory effect of dithiothretitol (DTT) and by the reciprocal selectivity of two structurally dissimilar non-peptide AII receptor antagonists.

DTT is an agent able to reduce disulfide bridges; by its disparate action on AII receptors in different tissues, DTT provided evidence of AII receptor heterogeneity. The non-peptide AII antagonists are denoted here as DuP 753 (the compound of Example 89 of EP 324377) and EXP-655 (the compound of Example 13 of EP 245637 and U.S. Pat. No. 4,812,462), which show reciprocal selectivity for the two subtypes. Using radioligand-receptor binding techniques, DuP 753 was found to be highly specific for an AII receptor site, designated AII receptor subtype-1 or AT$_1$, displaying an inhibitory constant IC$_{50}$ value of about $5 \times 10^{-9}$ M in rat adrenal cortex. This type of AII receptor was particularly sensitive to inactivation by DTT. EXP-655 exhibited very low affinity for the AT$_1$ site (IC$_{50}$ value of about $3.0 \times 10^{-4}$ M), but was highly selective for a distinct AII receptor site, designated AII receptor subtype-2 or AII2, exhibiting an inhibitory constant IC$_{50}$ value of about $1.0 \times 10^{-7}$ M in rat adrenal cortex. In contrast to the AT$_1$ receptor, the AT$_2$ receptor was resistant to DTT inactivation. Moreover, DuP 753 had very low affinity for the AT$_2$ receptor (IC$_{50}$ of about $1.4 \times 10^{-4}$ M). These two AII binding sites were thus shown to represent distinct subtypes of functional AII receptors. The antagonist specificity of the AT$_1$ and AT$_2$ receptor subtypes in rat adrenal cortex microsomes is summarized in Table 13. Whitebread et al. (Biochem. Biophys. Res. Comm. 163:284–291 (1989)) report two AII receptor subtypes, designated A and B. DTT is reported to inhibit binding to subtype B, but to enhance binding to subtype A.

We discovered that the rat adrenal medulla and brain contain a relatively high density of AII receptors which are predominantly the AT$_2$ subtype. EXP-655 displaced the [$^{125}$I]AII binding in rat brain membranes in a concentration-dependent manner yielding an IC$_{50}$ value of $3.2 \times 10^{-7}$ M. In contrast, DuP 753 displaced the binding of AII inefficiently, with an IC$_{50}$ value of $1.5 \times 10^{-4}$ M. Since the AT$_2$ receptor subtype is predominant in the brain, relative to the AT$_1$ receptor, EXP-655 and related compounds should be the preferred AII receptor blockers for inhibiting adverse effects mediated by AII in the central nervous system (CNS). Such highly selective $AT_2$-specific antagonists will not interfere with effects mediated by the $AT_1$ receptor.

The distribution of $AT_1$ and $AT_2$ receptors in certain regions of the brain was determined by the binding of AII to different sections of brain slices. The results indicate that there are clusters of DTT-sensitive, DuP 753-sensitive, AII binding sites ($AT_1$); however, the majority of AII binding sites in the brain are DTT-insensitive, EXP-655-sensitive, corresponding to $AT_2$ sites.

Our results show that AII binds to two distinct populations of AII receptors with similar affinity. These two receptor subtypes are not readily distinguishable by profiling with AII peptide homologs and analogs, but are identifiable by the use of the non-peptide antagonists, DuP 753 and EXP-655.

The physiological and clinical relevance of the CNS renin-angiotensin system are beginning to be appreciated by the use of orally active angiotensin-converting enzyme (ACE) inhibitors. ACE inhibitors may interfere with the metabolism of other peptide hormones, such as bradykinin, substance P, neurotensin, LHRH, TRH, and vasopressin, in addition to AII. Thus, although a possible role of ACE inhibitors in enhancing cognition has been reported, it was not predictable that AII receptor antagonists would also be useful in enhancing cognitive function. Moreover, it was not known which type of non-peptide AII receptor antagonist should be used, if any, in view of the heterogeneity in antagonist specificity exhibited by AII receptor.

In light of our discovery that the brain is enriched with the $AT_2$ receptor subtype, we expect that non-peptide $AT_2$ receptor antagonists, or receptor antagonists which show affinity for both $AT_1$ and $AT_2$ receptors, may be useful for certain $AT_2$ induced or mediated disorders of the CNS, such as cognitive dysfunction, schizophrenic polydipsia, centrally induced hypertension, diabetic nephropathy, and excessive milk production.

The human kidney has $AT_1$ and $AT_2$ receptors (Grone H.-J., Simon M. and Fuchs E. Autoradiographic characterization of angiotensin receptor subtypes in fetal and adult human kidney. *Am. J. Physiol.* 262: F326–F331, 1992). The $AT_2$ receptors were only found in preglomerular blood vessels whereas $AT_1$ in all other vessels and tubules. Thus, an $AT_2$ receptor antagonist may be useful to improve glomerular filtration by relaxing preglomerular vessels during arterial hypotension such as shock.

$AT_2$ receptors were found in cerebral arteries (Tsutsumi K. and Saavedra J. M. Charaterization of $AT_2$ angiotensin II receptors in rat anterior cerebral arteries *Am. J. Physiol.* 261:H667–H670, 1991). As migraine headaches may be induced by vasodilation of cerebral arteries and AII dilates cerebral arteries, it is conceivable that $AT_2$ antagonists may be useful for the treatment of migraine headaches.

The DuP 753-sensitive AII receptors have been characterized by an extensive series of non-peptide AII receptor antagonists (for example, co-assigned, co-pending U.S. patent application Ser. No. 07/279,194, filed Dec. 6, 1988, now U.S. Pat. No. 5,138,069; European Patent Application EP 0324377, published Jul. 19, 1989), in which the structure-affinity relationships observed in adrenal cortical microsomes correlate with vascular inhibitory potency and antihypertensive activity (Chiu et al. (1989) *J. Pharmacol. Exp Ther.* 250:867–874; Chiu et al. (1989) *Hypertension* 14:358). Thus, DuP 753 appears to be a highly specific AII blocker for the type of receptors that mediate $Ca^{+2}$-translocation. The discovery of a receptor ligand, EXP-655, for the DuP 753-insensitive sites establishes the identification of a new subtype of AII receptor which is distinct from those sensitive to DuP 753. The high selectivity exhibited by each receptor antagonist towards the respective receptor subtype (3500 to 10,000-fold difference in affinity) enables us to use these blockers as pharmacological or biochemical tools for receptor identification in various target organs. A survey of receptor tissue distribution using radioligand-receptor binding techniques indicates that rat vascular tissues and liver express predominantly the $AT_1$ receptors, while rat adrenal medulla and brain harbor primarily the $AT_2$ subtype. The rat adrenal cortex contains both types of receptor.

EXP 655 has been shown to block the effects of $AT_1$ 1) to increase potassium current in cultured neurones, 2) to produce pial arteriolar dilation in rat cranial windows, 3) to produce angiogenesis in chick chorioallantoic membranes and 4) to inhibit collagenase activity in cultured cardiac fibroblasts. These data suggest additional indications such as cerebral vasodilation, antiangiogenesis and cardiac remodeling in heart failure.

METHODS AND MATERIALS

Materials

The compounds designated DuP 753 and EXP-655 are synthesized according to procedures described by Carini and Duncia (European Patent Application EP 0253310 and EP 0324377) and by Blankley et al. (European Patent Application EP 0245637, to Warner-Lambert, filed Nov. 19, 1987), respectively. Saralasin, AI, AII, AIII, and dithiothreitol (DTT) were purchased from Sigma Chemical Co. (St. Louis, Mo.). [125I]AII was obtained from Du Pont-NEN Products (Boston, Mass.).

Procedures for the preparation of adrenal cortical microsomes and details of the binding assays are described in Chiu et al. (1989) *J. Pharmacol. Exp. Ther.* 250:867–874. The same procedures and conditions were used for adrenal medullary microsomes. In brief, aliquots of a freshly prepared particulate fraction (13,000–102,000 g) were incubated with 0.05 nM [125I-]AII and varying concentrations of inhibitor in a final volume of 0.5 mL of assay buffer containing 5 mM $MgCl_2$, and 50 mM Tris base, pH 7.2 at 25° C. After 60 min. of incubation, the reaction was terminated by addition of cold assay buffer. The bound and free radioactivity were rapidly separated through glass-fiber filters, and the trapped radioactivity was determined by gamma counting. All data presented are specific binding, which is defined as that which is displaced by 1 μM unlabeled AII added to the mixture.

To examine the effect of DTT on the subtypes of AII receptor, rat adrenal cortical membranes (600–20,000 g fraction) were prepared according to procedures described by Douglas et al. (1978) *Endocrinol.* 102:685–696, except the above binding assay conditions were used. The membrane preparations were either treated with buffer or 5 mM DTT for 30–40 min. before addition of other competing ligands.

AII receptor binding in rat smooth muscle cells and in rat brain were examined using procedures described by Chiu et al. (1989) *J. Pharmacol. Exp. Ther.* 250:867-874 and by Bennett and Snyder (1976) *J. Biol. Chem.* 254:7423-7430, respectively.

Autoradiography

Fresh tissue was frozen on powdered dry ice and stored at $-70°$ C. until used. Sections were cut at 15 microns and thaw mounted onto gelatin subbed slides. The AII binding was performed according to the procedures of Gehlert et al. (1986) *Neurosci.* 18:837-856, except that the DTT was omitted from the buffer and the incubation with radioiodinated AII was 60 min. Slides were placed under X-ray film (Kodak XAR-5) and exposed for 1½ days before processing the film to produce the film autoradiograms. The slides were then fixed with paraformaldehyde vapor at 80° C. for two hours, dried under air, delipidated, and dipped in emulsion (Kodak NTB-2). The coated slides were exposed for 4-5 weeks, developed with Kodak D-19 and counter-stained with hemotoxylin-eosin to view the histology.

Identification Of The Distinct Angiotension II Receptor Subtypes

The identification of distinct AII receptor subtypes was revealed by the use of two structurally dissimilar, non-peptide compounds, DuP 753 and EXP-655, that were found to show reciprocal selectivity for the two subtypes. In the rat adrenal cortex, DuP 753 inhibited 80% of the total AII binding with an IC$_{50}$ value on the sensitive sites of about $5 \times 10^{-9}$ M, while EXP-655 displaced only 20%. In the rat adrenal medulla, EXP-655 gave 90% inhibition of AII binding with an IC$_{50}$ value of about $3.0 \times 10^{-8}$ M, while DuP 753 was essentially inactive as an antagonist. The combination of the two compounds completely inhibited AII binding in both tissues.

The AII receptors of adrenal cortical microsomes have been previously characterized in terms of the binding affinities of a variety of angiotensin peptides (Saltman et al. (1976) *Endocrinology* 98:894903; Chiu et al. (1989) *FASEB J.* 3:A732) and nonpeptide AII receptor antagonists (Chiu et al. (1989) *J. Pharmacol. Exp. Ther.* 250:867-874).

Saralasin, a peptide analog of AII, is a potent and specific AII antagonist which blocks all known AII receptors, inhibits the specific binding of [$^{125}$I]AII to rat adrenal cortical microsomes in a concentration-dependent, monophasic fashion, yielding an IC$_{50}$ value of $1.0 \times 10^{-9}$ M. Complete displacement of AII was achieved at a concentration of $1 \times 10^{-7}$ M. In contrast, DuP 753 exhibited a biphasic displacement of [$^{125}$I]AII, inhibiting the specific binding of [1251]AII in a concentration-dependent manner over a range from $10^{-9}$ M to $10^{-7}$ M. A plateau of constant binding (about 28% of the total receptor-bound AII) existed over a twolog concentration increase of DuP 753, beyond which another concentration-dependent displacement was observed. Approximated IC$_{50}$ values for these two sites were about $5 \times 10^{-9}$ M and $1 \times 10^{-4}$ M. These results indicate the presence of two distinct AII receptors characterized as either DuP 753-sensitive or DuP 753insensitive.

In rat adrenal cortical microsomes, EXP-655 (compound #13 of European Patent Application EP 0245637, to Warner-Lambert) inhibited only 20% of the total specific AII binding at $3 \times 10^{-5}$ M. This result was puzzling because EXP-655 was reported to be an antihypertensive agent possessing high affinity for AII receptors (U.S. Pat. No. 4,812,462). On the contrary, however, we have found that this compound is inactive in antagonizing AII-induced rabbit aortic contractions at concentrations of up to $10^{-5}$ M and in lowering blood pressure in renal artery-ligated hypertensive rats at doses up to 30 mg/kg, administered IV.

We investigated whether the DuP 753insensitive sites were sensitive to EXP-655. To test this, the ligand-binding profile of the DuP 753-insensitive site was examined in the presence of a saturating concentration ($10^{-5}$ M) of DuP 753. This residual DuP 753-insensitive AII binding (expressed as 100%) was inhibited by saralasin and by EXP-655, in a concentration-dependent monophasic manner, with IC$_{50}$ values of about $1.3 \times 10^{-9}$ M and $1.0 \times 10^{-7}$ M, respectively. As expected, DuP 753 inhibited the residual binding only at high concentrations, with an IC$_{50}$ value of about $1.4 \times 10^{-4}$ M.

In view of the specificity displayed by EXP-655 for the DuP 753-insensitive sites, the ligand profile of DuP 753-sensitive site was reassessed in the presence of $10^{-5}$ M EXP-655. Saralasin and AII inhibited the specific binding as expected with IC$_{50}$ values of about 1.7 and $2.3 \times 10^{-9}$, respectively. In contrast to the result in the absence of EXP-655, DuP 753 now displayed a concentration dependent monophasic inhibition, eliminating essentially all AII binding, with an IC$_{50}$ of about $1.2 \times 10^{-3}$ M. As expected, EXP-655 was rather inactive under this condition, inhibiting the binding only at very high concentrations, with an IC$_{50}$ of about $3.0 \times 10^{-4}$ M.

The selectivity of each ligand for its respective receptor is presented as a ratio between the IC$_{50}$ obtained for the DuP 753-sensitive sites (AT$_1$) over that for the EXP-655-sensitive sites (AT$_2$). The results show that DuP 753 is about 10,000-fold more selective for the AT$_1$ receptors, whereas EXP-655 has about 3500-fold higher affinity for AT$_2$ receptors. In contrast, the peptide agonist (AII) and antagonist (saralasin) exhibit no preference for one AII receptor subtype relative to the other subtype. The antagonist specificity of the AT$_1$ and AT$_2$ receptor subtypes in rat adrenal cortex microsomes is summarized in Table 13.

TABLE 13

| Antagonist Specificity Exhibited by AII Receptor Subtypes | | |
|---|---|---|
| | IC$_{50}$ (M) | |
| Compound | AT$_1$ | AT$_2$ |
| AII | $2.3 \times 10^{-9}$ | $9.0 \times 10^{-10}$ |
| Saralasin | $1.7 \times 10^9$ | $1.3 \times 10^{-9}$ |
| Example 25 | $>10^{-5}$ | $6 \times 10^{-8}$ |
| Example 32 | $>10^{-5}$ | $7.0 \times 10^{-8}$ |
| DuP 753 | $5 \times 10^{-9}$ | $1.4 \times 10^{-4}$ |
| EXP-655 | $3.0 \times 10^{-4}$ | $1.0 \times 10^{-7}$ |

AT$_1$ site binding was determined in the presence of $10^{-5}$ M EXP-655. AT$_2$ site binding was determined in the presence of $10^{-5}$ M DuP 753. IC$_{50}$ was determined by displacement of [$^{125}$I]AII from the receptor by the indicated compound. The compounds of this application, designated Example 2 and Example 27, are seen to bind selectively to AT$_2$ receptors. These compounds are expected to be useful in disease states mediated by AT$_2$ receptors and responsive to blockers of the AT$_2$ receptor, including CNS disorders.

Distribution of AII Receptor Subtypes

Autoradiographic examination of [$^{125}$I]AII binding to the rat adrenal gland was undertaken to explore the localization of AII receptors and possible anatomical differentiation of subtypes. [$^{125}$I]AII densely labeled the outer layers of the adrenal cortex as well as the entire adrenal medulla, as reported by Catt et al. (1984) *J. Cardiovasc. Pharmacol.* 6:S575S586. Most of the cortical labeling appeared to be over the zona glomerulosa with moderate labeling of zona fasciculata. Unlabeled AII potently inhibited the labeling in both cortex and medulla. In the presence of $10^{-6}$ M DuP 753, the labeling over the cortex was significantly reduced and the resistant sites were found to be distributed uniformly around the outer layer of the cortex. The labeling of the adrenal medulla, however, was not appreciably affected by DuP 753. By contrast, $10^{-6}$ M EXP-655 had no apparent effect on cortical labeling, but almost totally eliminated the labeling of the medulla. When both compounds were applied in combination, the AII labeling of both regions was completely abolished.

The results show that DuP 753-resistant AT$_2$ receptor sites are present in the cortical zona glomerulosa and predominate in the medulla of the rat adrenal gland. To characterize these AII receptors further, [$^{125}$I]AII specific binding to rat adrenal medullary microsomes was studied. Saralasin inhibited the binding in a concentration-dependent fashion with an IC$_{50}$ value of $4 \times 10^{-10}$ M. About 90% of the total binding was resistant to displacement by DuP 753 which is consistent with the results obtained by autoradiographic techniques. In contrast, the inhibition by EXP-655 was concentration-dependent and nearly monophasic, yielding an IC$_{50}$ value of $3 \times 10^{-8}$ M. Interestingly, 10% of the binding was resistant to EXP-655, which complements the 10% inhibition seen with DuP 753 below $1 \times 10^{-6}$ M.

The present studies using radioligand binding and autoradiographic techniques clearly demonstrate the existence of two subtypes of AII receptors in the rat adrenal gland. The adrenal cortex, particularly the zona glomerulosa, contains predominantly the DuP 753-sensitive AT$_1$ receptor, whereas the medulla harbors almost exclusively the DuP 753-insensitive, EXP-655-sensitive type of AII receptor (AT$_2$). Rat aortic smooth muscle cells were found to display primarily the DuP 753-sensitive AII binding sites (AT$_1$), in contrast to the rat adrenal medulla and brain, which are dominated by DuP 753-insensitive, EXP-655-sensitive AII binding sites (AT$_2$).

Discrimination of AII Receptor Subtype by DTT Sensitivity

The following studies were designed to examine whether DTT could differentiate the AT$_1$ and AT$_2$ subtypes of AII receptor. The differential effect of DTT on AII receptors in rat liver was previously reported by Gunther et al. (1984) *J. Biol. Chem.* 259:7622-7629. AII receptors obtained from a 600-20,000 g fraction of adrenal cortical membranes were pretreated with and without 5 mM DTT for 30 min. at room temperature before addition of ligands.

The inhibitory potency of AII was enhanced 2.5-fold in the presence of DTT, with an IC$_{50}$ of $1 \times 10^{-9}$ M in the absence of DTT and an IC$_{50}$ of $0.4 \times 10^{-9}$ M in the presence of DTT. Saralasin inhibition was not significantly altered by DTT. In contrast, the inhibitory effect of DuP 753 at concentrations between $3 \times 10^{-9}$ to $3 \times 10^{-6}$ M was essentially abolished in the presence of DTT. On the other hand, DTT transformed EXP-655 from a weak to a potent inhibitor, displacing the binding in a concentration-dependent and nearly monophasic fashion, yielding an apparent IC$_{50}$ value of $2.5 \times 10^{-7}$ M. Thus, the DTT-insensitive site shows very low affinity for DuP 753. These data indicate that the DuP 753-sensitive receptors (AT$_1$) are inactivated by DTT and the remaining DTT-resistant sites are the EXP655-sensitive AT$_2$ receptors.

Dosage Forms

The compounds of this invention can be administered for the treatment of AT$_2$ mediated CNS disorders and other AT$_2$ receptor mediated disorders by any route and dosage form that effects contact of the active ingredient compound with the site of action in the body of a warm-blooded animal. For example, administration can be parenteral, i.e., subcutaneous, intravenous, intramuscular, or intraperitoneal. Alternatively, or concurrently, in some cases administration can be by the oral route, or topically, e.g., for the treatment of glaucoma.

The compounds can be administered by any conventional means available for use with pharmaceuticals, either as individual therapeutic agents or as part of a combination of therapeutic agents. They can be administered alone, but are generally administered with a pharmaceutical carrier selected on the basis of the chosen route of administration and standard pharmaceutical practice.

Reference to the compounds of this invention includes pharmaceutically acceptable acid addition salts, base salts, and N-oxide derivatives thereof. By the term "pharmaceutically acceptable acid addition salt" is meant any non-toxic pharmaceutically suitable salt of a compound described above which has the desired pharmacological properties in mammals. Preparation of such salts is well know to those skilled in the pharmaceutical sciences. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate, and pamoate. Methods for preparation of N-oxide derivatives are also well known in the art. Examples of inorganic bases suitable for the formation of compounds of this invention include, e.g., the hydroxides, carbonates, and bicarbonates of ammonia, sodium, lithium, potassium, calcium, magnesium, aluminum, and zinc. Pharmaceutically acceptable base addition salts of the compounds of the invention may also be formed with suitable organic bases that are nontoxic and strong enough to form such salts, as is readily understood by those of ordinary skill in the art. See, e.g., "Pharmaceutical Salts", *J. Pharm. Sci.* 66 (1):1-19 (1977).

For the purpose of this disclosure, a warmblooded animal is a member of the animal kingdom possessed of a homeostatic mechanism, preferably a mammal.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water for injection, a suitable oil, saline, aqueous dextrose (glucose), and related sugar solutions and glycols such as propylene glycol or polyethylene glycols are suitable carriers for parenteral solutions. Solutions for parenteral administration must be sterile and nonpyrogenic and will preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Information about suitable pharmaceutical carriers and formulations may be found, e.g., in various editions of *Remington's Pharmaceutical Sciences*, Mack Publishing Company, or of the USP/NF.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets is prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injection

A parenteral composition suitable for administration by injection is prepared by stirring 1.5% by weight of active ingredient in 10% by volume propylene glycol.

The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered in conjunction with another therapeutic agent. When the drugs are administered in physical combination, the dosage form and administration route should be selected for compatibility with both drugs.

What is claimed is:

1. A compound of the formula:

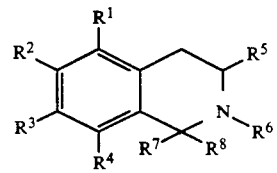

wherein
R$^1$ and R$^2$ are independently hydrogen, alkyl of from 1 to 5 carbon atoms, cycloalkyl of from 3 to 7 carbon atoms, (CH$_2$)$_m$ cycloalkyl where m is 1-4 and the cycloalkyl portion is of from 3 to 7 carbon atoms, —OR$_y$, where R$_y$ is H, alkyl of from 1 to 4 carbon atoms, phenyl or benzyl, perfluoroalkyl of from 3 to 7 carbon atoms, or

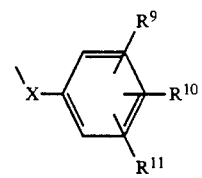

except that R$^1$ and R$^2$ cannot both be hydrogen at the same time;
R$^3$ and R$^4$ are independently hydrogen, alkoxy of rom 1 to 5 carbon atoms, hydroxy, alkyl of from 1 to 5 carbon atoms, bromine, chlorine, or S(O)$_p$alkyl where p is 0–2 and the alkyl portion is of from 1 to 5 carbon atoms;
R$^5$ is —CO$_2$R$^{12}$, —CH$_2$OH, —CHO, —CONHOR$^{12}$, —NHSO$_2$CF$_3$, or

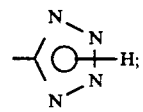

R$^6$ is —COCHR$^{15}$R$^{16}$ or —CONR$^{14}$R$^{17}$;
R$^7$ and R$^8$ are independently hydrogen, or alkyl of from 1 to 5 carbon atoms;
R$^9$, and R$^{10}$, and R$^{11}$ are independently hydrogen, alkyl of from 1 to 5 carbon atoms, phenyl, hydroxy, alkoxy of from 1 to 5 carbon atoms, —NO$_2$, —NR$^{12}$R$^{13}$, —NR$^{12}$COR$^{13}$, fluorine, chlorine, bromine, iodine, —COR$^{14}$, —CF$_3$, or —SR$^{12}$;

$R^{12}$ and $R^{13}$ are independently hydrogen, alkyl of from 1 to 5 carbon atoms, or phenyl;

$R^{14}$ is hydrogen, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{15}$ and $R^{16}$ are independently cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{17}$ is alkyl of from 1 to 5 carbon atoms, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

X is —CH$_2$)$_n$— where n is 0 to 5, —O—, —CO—, —S—, —(CH=CH)—, —NR$^{12}$CO—, —CONR$^{12}$—, —CH$_2$O—, —OCH$_2$—, —SCH$_2$—, —CH$_2$S—. A compound of claim 1 wherein:

$R^3$ and $R^4$ are hydrogen;

$R^7$ and $R^8$ are hydrogen;

$R^{14}$ is cycloalkyl of from 3 to 7 carbon atoms, phenyl, or phenyl monosubstituted with alkyl of from 1 to 5 carbon atoms, hydroxy, alkoxy of from 1 to 4 carbon atoms, halogen, —CN, —NO$^2$, or —NR$^{12}$R$^{13}$.

2. A Compound of claim 1 wherein:

$R^1$ and $R^2$ are as in claim 1 except that $R^1$ and $R^2$ are not both hydrogen at the same time $R^3$ and $R^4$ are hydrogen;

$R^7$ and $R^8$ are hydrogen;

$R^{14}$ is cycloalkyl of from 3 to 7 carbon atoms, phenyl, or phenyl monosubstituted with alkyl of from 1 to 5 carbon atoms, hydroxy, alkoxy of from 1 to 4 carbon atoms, halogen, —CN, —NO$^2$, or —NR$^{12}$R$^{13}$.

3. A compound of claim 1 which is 2-Diphenylacetyl-5-benzyl-1,2,3,4-tetrahydroisoquinoline-3-carboxylic acid.

4. A compound of claim 1 which is 2-Diphenylacetyl-5-phenyl-1,2,3,4-tetrahydroisoquinoline-3-carboxylic acid.

5. A compound of claim 1 which is 2-Diphenylacetyl-5-(p-methoxyphenyl)methyl-1,2,3,4-tetrahydro-isoquinoline-3-carboxylic acid.

6. A compound of claim 1 which is 2-Diphenylacetyl-5-(p-methoxyphenyl)-1,2,3,4-tetrahydro-isoquinoline-3-carboxylic acid.

7. A compound of claim 1 which is 2-(N-methyl-N-phenylcarbamoyl)-5-(p-methoxyphenyl)methyl-1,2,3,4-tetrahydroisoquinoline-3-carboxylic acid.

8. A compound of claim 1 which is 2-(N,N-Diphenylcarbamoyl)-5-(p-methoxyphenyl)methyl-1,2,3,4-tetrahydroisoquinoline-3-carboxylic acid.

9. A compound of claim 1 which is 2-Diphenylacetyl-6-phenoxy-1,2,3,4-tetrahydroisoquinoline-3-carboxylic acid.

10. A compound of claim 1 which is 2-Diphenylacetyl-6-phenyl-1,2,3,4-tetrahydroisoquinoline-3-carboxylic acid.

11. A compound of claim 1 which is 2-Diphenylacetyl-5-phenoxy-1,2,3,4-tetrahydroisoquinoline-3-carboxylic acid.

12. A pharmaceutical composition comprising a suitable pharmaceutical carrier and a therapeutically effective amount of a compound of claim 1.

13. A pharmaceutical composition comprising a suitable pharmaceutical carrier and a therapeutically effective amount of a compound of claim 2.

14. A method for the treatment of a disorder or a condition in a mammal mediated by AT$_2$ receptors comprising administering to the mammal a therapeutically effective amount of a compound of the formula:

wherein $R^1$ and $R^2$ are independently hydrogen, alkyl of from 1 to 5 carbon atoms, cycloalkyl of from 3 to 7 carbon atoms, (CH$_2$)$_m$ cycloalkyl where m is 1–4 and the cycloalkyl portion is of from 3 to 7 carbon atoms, —ORy, where Ry is H, alkyl of from 1 to 4 carbon atoms, phenyl or benzyl, perfluoroalkyl of from 3 to 7 carbon atoms, or $R^3$ and $R^4$ are independently hydrogen, alkoxy of from 1 to 5 carbon atoms, hydroxy, alkyl of from 1 to 5 carbon atoms, bromine, chlorine, or S(O)$_p$alkyl where p is 0–2 and the alkyl portion is of from 1 to 5 carbon atoms;

$R^5$ is —CO$_2$R$^{12}$, —CH$_2$OH, —CHO, —CONHOR$^{12}$, —NHSO$_2$CF$_3$, or $R^6$ is —COCHR$^{15}$R$^{16}$ or —CONR$^{14}$R$^{17}$;

$R^7$ and $R^8$ are independently hydrogen, or alkyl of from 1 to 5 carbon atoms;

$R^9$, and $R^{10}$, and $R^{11}$ are independently hydrogen, alkyl of from 1 to 5 carbon atoms, phenyl, hydroxy, alkoxy of from 1 to 5 carbon atoms, —NO$_2$, —NR$^{12}$R$^{13}$, —NR$^{12}$COR$^{13}$, fluorine, chlorine, bromine, iodine, —COR$^{14}$, —CF$^3$, or —SR$^{12}$;

$R^{12}$ and $R^{13}$ are independently hydrogen, alkyl of from 1 to 5 carbon atoms, or phenyl;

$R^{14}$ is hydrogen, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{15}$ and $R^{16}$ are independently cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{17}$ is alkyl of from 1 to 5 carbon atoms, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

X is —CH$_2$)$_n$— where n is 0 to 5, —O—, —CO—, —S—, —(CH=CH)—, —NR$^{12}$CO—, —CONR$^{12}$—, —CH$_2$O—, —OCH$_2$—, —SCH$_2$—, —CH$_2$S—.

15. The method of claim 14 wherein the compound of the formula is the same as in claim 14, except that $R^1$ and $R^2$ are not both hydrogen at the same time;
$R^3$ and $R^4$ are hydrogen;
$R^7$ and $R^8$ are hydrogen;
$R^{14}$ is cycloalkyl of from 3 to 7 carbon atoms, phenyl, or phenyl monosubstituted with alkyl of from 1 to 5 carbon atoms, hydroxy, alkoxy of from 1 to 4 carbon atoms, halogen, —CN, —NO$^2$, or —NR$^{12}$R$^{13}$.

16. A method for the treatment of cognitive or neurological dysfunction mediated by AII in a mammal comprising administering to the mammal a therapeutically effective amount of a compound of the formula:

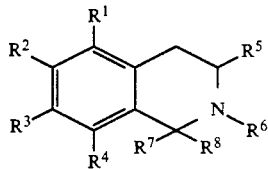

wherein $R^1$ and $R^2$ are independently hydrogen, alkyl of from 1 to 5 carbon atoms, cycloalkyl of from 3 to 7 carbon atoms, (CH$_2$)$_m$ cycloalkyl where m is 1–4 and the cycloalkyl portion is of from 3 to 7 carbon atoms, —OR$_y$, where R$_y$ is H, alkyl of from 1 to 4 carbon atoms, phenyl or benzyl, perfluoroalkyl of from 3 to 7 carbon atoms, or

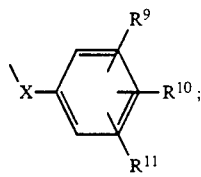

$R^3$ and $R^4$ are independently hydrogen, alkoxy of from 1 to 5 carbon atoms, hydroxy, alkyl of from 1 to 5 carbon atoms, bromine, chlorine, or S(O)$_p$alkyl where p is 0-2 and the alkyl portion is of from 1 to 5 carbon atoms;

$R^5$ is —CO$_2$R$^{12}$, —CH$_2$OH, —CHO, —CONHOR$^{12}$, —NHSO$_2$CF$_3$, or

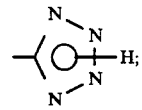

$R^6$ is —COCHR$^{15}$R$^{16}$ or —CONR$^{14}$R$^{17}$;

$R^7$ and $R^8$ are independently hydrogen, or alkyl of from 1 to 5 carbon atoms;

$R^9$, and $R^{10}$, and $R^{11}$ are independently hydrogen, alkyl of from 1 to 5 carbon atoms, phenyl, hydroxy, alkoxy of from 1 to 5 carbon atoms, —NO$_2$, —NR$^{12}$R$^{13}$, —NR$^{12}$COR$^{13}$, fluorine, chlorine, bromine, iodine, —COR$^{14}$, —CF$^3$, or —SR$^{12}$;

$R^{12}$ and $R^{13}$ are independently hydrogen, alkyl of from 1 to 5 carbon atoms, or phenyl;

$R^{14}$ is hydrogen, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{15}$ and $R^{16}$ are independently cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

$R^{17}$ is alkyl of from 1 to 5 carbon atoms, cycloalkyl of from 3 to 7 carbon atoms, phenyl, phenyl monosubstituted with alkyl of from 1 to 5 carbon atoms, hydroxy, alkoxy of from 1 to 5 carbon atoms, halogen, —CN, —NO$_2$, or —NR$^{12}$R$^{13}$;

X is —CH$_2$)$_n$— where n is 0 to 5, —O—, —CO—, —S—, —(CH=CH)—, —NR$^{12}$CO—, —CONR$^{12}$—, —CH$_2$O—, —OCH$_2$—, —SCH$_2$—, —CH$_2$S—.

17. The method of claim 16 wherein the compound of the formula is the same as in claim 16, except that $R^1$ and $R^2$ are not both hydrogen at the same time;
$R^3$ and $R^4$ are hydrogen;
$R^7$ and $R^8$ are hydrogen;
$R^{14}$ is cycloalkyl of from 3 to 7 carbon atoms, phenyl, or phenyl monosubstituted with alkyl of from 1 to 5 carbon atoms, hydroxy, alkoxy of from 1 to 4 carbon atoms, halogen, —CN, —NO$^2$, or —NR$^{12}$R$^{13}$.

* * * * *